US00PP09184P

United States Patent [19]

van der Meer

[11] Patent Number: Plant 9,184

[45] Date of Patent: Jul. 4, 1995

[54] HYBRID TEA ROSE PLANT NAMED 'SELLOBBY'

[75] Inventor: Peter J. A. van der Meer, Carlsbad, Calif.

[73] Assignee: Terra Nigra B.V., De Kwakel, Netherlands

[21] Appl. No.: 105,355

[22] Filed: Aug. 11, 1993

[51] Int. Cl.[6] ..... A01H 5/00

[52] U.S. Cl. ..... Plt./18

[58] Field of Search ..... Plt. 18, 11

[56] References Cited

U.S. PATENT DOCUMENTS

P.P. 6,559 2/1989 Ohkawa ..... Plt./18

*Primary Examiner*—Howard J. Locker

[57] ABSTRACT

A new rose variety of the Hybrid Tea class, characterized by its continuous and profuse production of medium-sized soft pink flowers, borne singly on upright stems on a sturdy bush of medium height, having abundant and glossy foliage and a weak fragrance.

2 Drawing Sheets

BACKGROUND OF THE INVENTION

The present invention relates to a new and distinct variety of rose plant of the Hybrid Tea class, which was originated by me by crossing the variety "Jacaranda" with an unnamed (SR 85.055) and unpatented seedling.

The primary objective of this breeding was to obtain a new rose variety comparable to that of "Jacaranda" with a smaller in size and more soft pink flower and same fragrancy. While the results achieved a distinct pink hybrid tea rose of smaller size, the new variety did not otherwise correspond to the characteristics of "Jacaranda", but nevertheless, achieved a new and distinct combination of characteristics which is desirable and attractive, as well as different from anything heretofore available, as evidenced by the following characteristics which are outstanding in the new variety:

(1) a medium-sized soft pink flower
(2) very rapid flowering cycles
(3) distinctive fragrance
(4) a vigorous upright plant of medium height
(5) very glossy foliage The foregoing characteristics and distinctions definitely differentiate the new variety from its parents, as well as from all other varieties of which I am aware, and asexual reproduction of the new variety by cuttings, grafting or tissue culture as performed in a greenhouse in De Kwakel, the Netherlands, shows that these characteristics and distinctions come true to form and are established and transmitted through succeeding propagations.

BRIEF DESCRIPTION OF THE DRAWING

The new variety of rose plant is illustrated by the accompanying photographic illustrations, of which Sheet 1 shows a full face view of the flower and Sheet 2 shows typical specimens of the vegetative growth and flowers of the new variety in different stages of development. The color renditions are as nearly true as as it is possible to make same in color illustrations of this character by conventional photographic procedures.

The following is a detailed description of this new variety, with color terminology in accordance with The Royal Horticultural Society Colour Chart (R.H.S.C.C.). The terminology used in the colordescription herein refers to plate numbers in the aforementioned color chart e.g. "53A" is plate "53A of The Royal Horticultural Society Colour Chart.

Parentage: Seedling.

*Seed parent.*—"Jacaranda".

*Pollen parent.*—Unnamed Seedling (SR 85,055)

Classification:

*Botanic.*—Hybrid Tea.

*Commercial.*—Hybrid Tea.

BOTANICAL DESCRIPTIONS OF THE PLANT

Flower (Observations made from specimens grown in a greenhouse at De Kwakel, the Netherlands)

Blooming habit of Sellobby: Recurrent-continuous.

A. Bud:

(1) *Size.*—Medium. Diameter 2.0 cm. Length 2.5 cm.
(2) *Form.*—Pointed; is not affected by wet or hot weather.
(3) *Color.*—When the sepals first divide, the color of the outside is pink 55C.
(4) *Sepals.*—Slightly branched, stand up when petals begin to unfurl. Color: inside: green 138B. outside: green 144A.
(5) *Calyx.*—Color: green 143C. Shape: oval, pointed. Size: medium. Aspect: smooth. Odor when rubbed: weak.
(6) *Peduncle.*—Length: medium 6 cm. Aspect: prickled. Strength: good. Color: green 144A.
(7) *Opening.*—opens up well; is not affected by adverse weather.

B. Bloom:

(1) *Size.*—Medium when fully expended, about 9 cm in diameter with a depth of about 3 cm.
(2) *Borne.*—Single.
(3) *Stems.*—Length: medium. Strength: average.
(4) *Form (when first open).*—Cup-form. Permanence: will flatten when aging.
(5) *Petalage.*—Number of petals: 20–25.
(6) *Color.*—Center of flower; pink (56B). Outer petals: pink (56D). Base of petals: pink (56D). Inside of petals: pink (56D). Reverse of petals: yellow (56B). General tonality: yellow (56D).

(7) Discoloration.—General tonality at end of first day: Yellow (56B-C). Second day: fading to (56D). Third day; fading to (56D).

C. Petals:

(1) *Texture.*—Semi-leathery; not affected by wet or not weather.

(2) *Appearance.*—Inside: shiny. Outside: satiny.

(3) *Form.*—Round shaped.

(4) *Arrangement.*—Regular (5) *Petaloids in center.*—Few; small.

(6) *Persistence.*—Drop off cleanly.

(7) *Fragrance.*—Weak; fresh rose scent.

(8) *Lasting quality.*—On the plant — long. As cut flower — medium (9 days).

Reproductive Organs

Stamens, anthers:

*Size.*—Medium; regularly arranged around styles, average number about 130.

*Color.*—Light orange (19D).

Stamens, filaments (threads): Long, average about 10 mm in length.

*Color.*—Pink-red (49B).

Pollen:

*Color.*—Yellow (17B).

Styles: Bunched; uneven length; medium (about 5–6 mm) length; thin.

Stigmas:

*Color.*—Yellow (159A).

Ovaries: All enclosed in calyx; pitcher-shaped; about 9 mm through center diameter.

Hips:

*Color.*—Orange at maturity.

*Shape.*—Round with a flat base (about 2.5 cm×2.5 cm).

Resistancy: Normal resistance against mildew, white fly and red spider mixes; More sensitive to Californian thrips.

Plant

Form: Upright and branched.

Growth: Vigorous: upright: medim height average height after one year is 80–100 cm Foliage: Compound of 3, 5, or 7 leaflets; average leaflet length is about 6–9 cm, average size of compound leaf is about 15 cm in length.

(1) *Size.*—Average.

(2) *Quantity.*—Abundant.

(3) *Color.*—New foliage; upper side — green 139A. under side — green 138A. Old foliage: upper side — green 139A. under side — green 138A.

(4) *Shape.*—Oval and pointed.

(5) *Texture.*—Upper side — smooth and glossy.

(6) *Ribs and veins.*—Ordinary.

(7) *Edge.*—Serrated, saw toothed.

(8) *Serration.*—Single.

(9) *Leaf stem.*—Color: green 147B. Under side: prickly.

(10) *Stipules.*—Medium (about 3.5 cm) length: smooth.

Wood:

*New Wood.*—Color: bronze. Bark: smooth.

*Old wood.*—Color: green. Bark: smooth.

Thorns:

*Quantity.*—On main stalks from base: average. On laterals from stalk: average. Form: concave. Length: medium. Hooked: downward. Color (when young): green-bronze. Position: irregular.

Prickles:

*Quantity.*—On main stalks: few. On laterals: few.

Short needles:

*Quantity.*—On main stalks: none. On laterals: none.

I claim:

1. A new and distinct variety of rose plant of the Hybrid Tea class, substantially as herein shown and described characterized particularly as to novelty by its medium-size pink flowers, borne singly, with typical glossy foliage and very rapid flowering cycles.

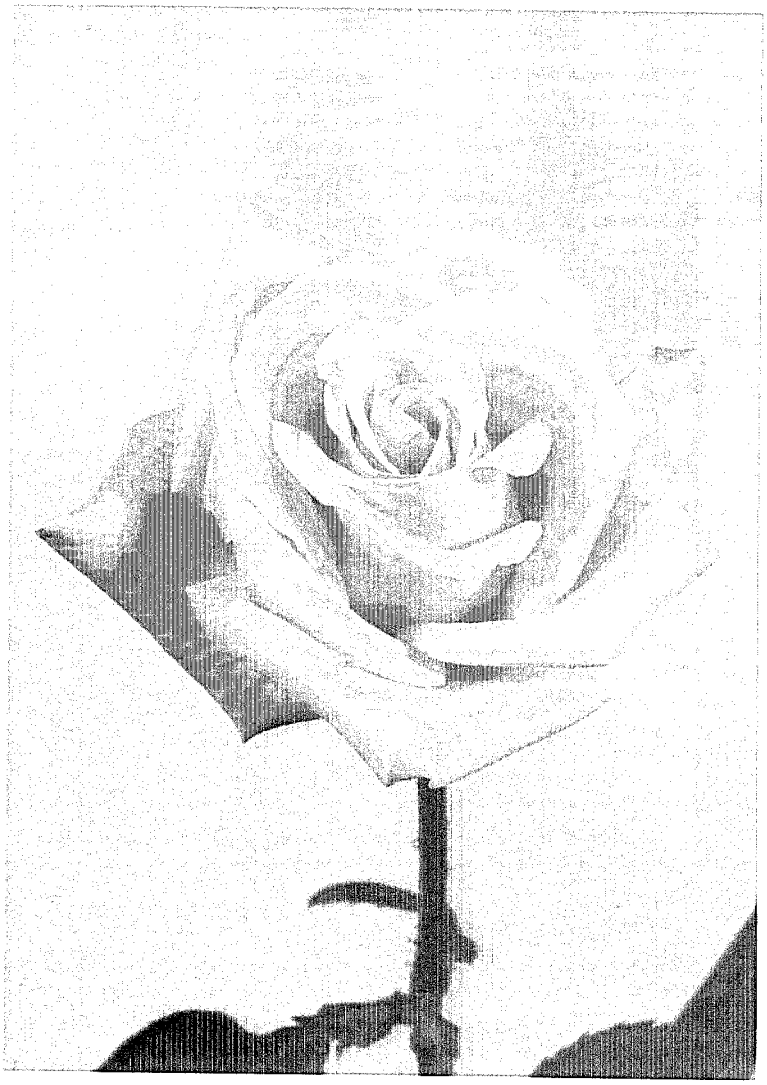

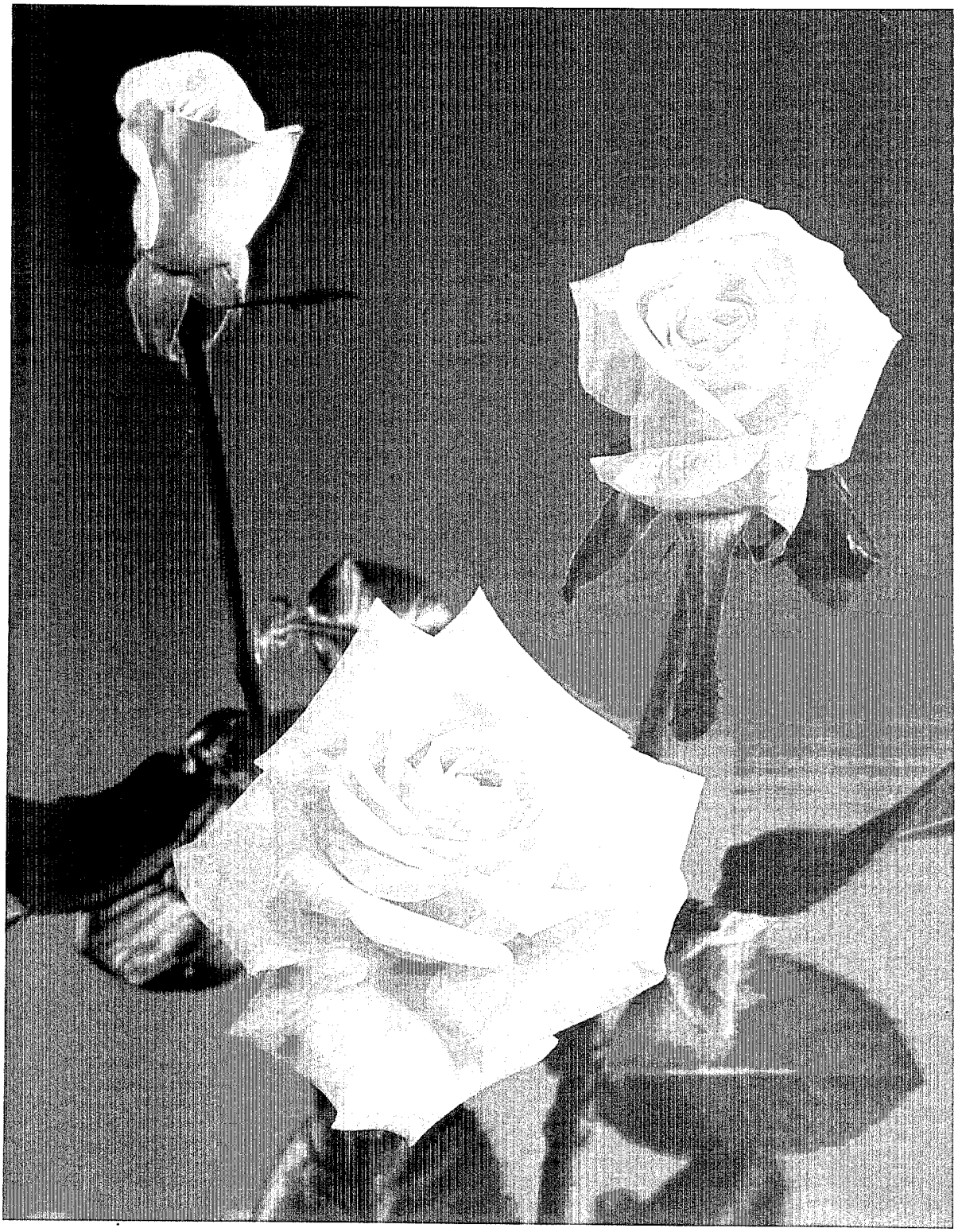

* * * * *